(12) United States Patent
Ahmad et al.

(10) Patent No.: US 9,964,533 B2
(45) Date of Patent: May 8, 2018

(54) SYSTEM FOR MEASURING MULTI-PHASE FLUID FLOW CHARACTERISTICS

(71) Applicant: KING FAHD UNIVERSITY OF PETROLEUM AND MINERALS, Dhahran (SA)

(72) Inventors: Aftab Ahmad, Dhahran (SA); Luai M. Alhems, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 95 days.

(21) Appl. No.: 14/940,101

(22) Filed: Nov. 12, 2015

(65) Prior Publication Data

US 2017/0138189 A1    May 18, 2017

(51) Int. Cl.
| | |
|---|---|
| *G01N 33/28* | (2006.01) |
| *E21B 49/08* | (2006.01) |
| *G01F 1/34* | (2006.01) |
| *G01F 1/684* | (2006.01) |
| *G01N 9/26* | (2006.01) |
| *G01N 9/36* | (2006.01) |

(52) U.S. Cl.
CPC ....... *G01N 33/2847* (2013.01); *E21B 49/086* (2013.01); *G01F 1/34* (2013.01); *G01F 1/684* (2013.01); *G01N 9/26* (2013.01); *G01N 9/36* (2013.01); *G01N 33/2823* (2013.01); *E21B 49/081* (2013.01); *E21B 2049/085* (2013.01)

(58) Field of Classification Search
CPC ..... E21B 2049/085; E21B 49/08; G01N 9/26; G01N 9/36; G01N 33/2823; G01N 33/28476
See application file for complete search history.

(56) References Cited

U.S. PATENT DOCUMENTS

| | | | |
|---|---|---|---|
| 7,059,199 B2 | 6/2006 | Mattar et al. | |
| 7,281,415 B2* | 10/2007 | Johansen | E21B 47/10 |
| | | | 73/61.45 |
| 7,484,426 B2 | 2/2009 | Evans et al. | |
| 7,661,302 B2 | 2/2010 | Gysling | |

(Continued)

FOREIGN PATENT DOCUMENTS

| | | |
|---|---|---|
| CN | 104101396 A | 10/2014 |
| CN | 104234691 A | 12/2014 |

*Primary Examiner* — Paul West
(74) *Attorney, Agent, or Firm* — Richard C. Litman (57) ABSTRACT

The system for measuring multi-phase fluid flow characteristics is an on-site system for measuring and calculating fluid density of a multi-phase fluid, such as a mixture of oil and water, as well as a water cut thereof. The system for measuring multi-phase fluid flow characteristics includes a conduit having a lower inlet and an upper outlet. The lower inlet is adapted for direct connection to an oil pipeline, an oil well, or the like for receiving the multi-phase fluid flowing therethrough. The conduit defines a pressure monitoring portion having opposing ends. First and second impulse lines connect first and second gauge pressure transmitters and a differential pressure transmitter to the opposing ends to measure total pressure drop and frictional pressure differential to an external controller, which calculates the fluid density and the water cut therefrom The system may also include temperature and volumetric flow rate sensors.

15 Claims, 5 Drawing Sheets

(56) References Cited

U.S. PATENT DOCUMENTS 7,963,172 B2 6/2011 Liu et al.
2014/0041463 A1 2/2014 Vethe et al.
2014/0355737 A1 12/2014 Korkin et al.

* cited by examiner

SYSTEM FOR MEASURING MULTI-PHASE FLUID FLOW CHARACTERISTICS

BACKGROUND OF THE INVENTION

1. Field of the Invention

The present invention relates to oil well monitoring equipment, and particularly to a system for measuring multi-phase fluid flow characteristics (such as fluid density, water cut, flow rate, etc.) in a multi-phase fluid, such as crude oil containing a mixture of oil and water, in pipes either down hole or at the surface of the well.

2. Description of the Related Art

When dealing with crude oil, either from an oil well or when the oil is still "down-hole" (i.e., still in an underground reservoir or the like), it is very important to be able to monitor and measure various fluid properties of the crude oil. This is relatively difficult at the crude oil stage, since crude oil is typically in the form of a multi-phase fluid, consisting of at least both oil and water. The multi-phase nature of the fluid makes accurate on-site monitoring of fluid mixture density, water content (or "water cut") and flow rate very difficult due to the fluid dynamics and complex makeup of the crude oil mixture.

Due to the inherent difficulties in making direct measurements from such a two-phase mixture, the oil and water are typically separated from one another before measurements are made. This, however, requires an interruption of the continuous industrial process of crude oil extraction. Additionally, a wide variety of devices must be used in such separation-based measurement, including, for example, both phase fraction and phase velocity measurement devices simply to measure the water content in the multi-phase fluid. It would obviously be desirable to be able to directly measure fluid properties of the multi-phase fluid with a single set of instruments and without having to first separate the oil from the water.

Thus, a system for measuring multi-phase fluid flow characteristics solving the aforementioned problems is desired.

SUMMARY OF THE INVENTION

The system for measuring multi-phase fluid flow characteristics is an on-site system for measuring and calculating a fluid density of a multi-phase fluid, $\rho_m$, such as a mixture of oil and water, as well as a water cut, $\lambda$, thereof. The system for measuring multi-phase fluid flow characteristics includes a substantially cylindrical conduit having a lower inlet and an upper outlet. The lower inlet is adapted for direct connection to an oil pipeline, an oil well, or the like for receiving a multi-phase fluid flowing therethrough. The substantially cylindrical conduit defines a diameter D and has an entrance portion adjacent the lower inlet, an exit portion adjacent the upper outlet, and a pressure monitoring portion positioned therebetween. The entrance portion has a length $L_e$ and the pressure monitoring portion has a length $L_p$.

A first gauge pressure sensor is mounted within the substantially cylindrical conduit at a boundary between the entrance portion and the pressure monitoring portion, such that the first gauge pressure sensor measures a first gauge pressure $GP_1$ of the mixture of oil and water flowing through the substantially cylindrical conduit. A second gauge pressure sensor is mounted within the substantially cylindrical conduit at a boundary between the pressure monitoring portion and the exit portion, such that the second gauge pressure sensor measures a second gauge pressure $GP_2$ of the mixture of oil and water flowing through the substantially cylindrical conduit.

A differential pressure transmitter is in communication with the first and second gauge pressure sensors by respective first and second impulse lines. The differential pressure transmitter measures a frictional pressure differential between the first and second gauge pressure sensors, $DP_f$, and a total pressure differential between the first and second gauge pressure sensors. The total pressure differential, $DP_T$, is simply the difference between gauge pressure measurements; i.e., $DP_T = GP_1 - GP_2$.

A temperature sensor is further mounted within the substantially cylindrical conduit in the exit portion thereof for measuring a temperature, T, of the multi-phase fluid. The first gauge pressure sensor, the second gauge pressure sensor, the differential pressure transmitter, and the temperature sensor are each in communication with a controller, e.g., a microcontroller. When the substantially cylindrical conduit is positioned vertically, the controller calculates the fluid density of the mixture of oil and water, $\rho_m$, as $\rho_m = (DP_T - DP_f)/L_p g$, where g is the gravitational acceleration constant near the Earth's surface (i.e., 9.8 m/s$^2$). In cases where the substantially cylindrical conduit is positioned at an angle $\theta$ with respect to a horizontal surface (such as the ground), the density is calculated using the vertical component of the gravitational contribution, i.e., $\rho_m = (DP_T - DP_f)/(L_p g \sin \theta)$.

The controller further calculates the water cut, $\lambda$, as $\lambda = (\rho_m - \rho_o)/(\rho_w - \rho_o)$, where $\rho_o$ is a density of the oil of the mixture of oil and water at the temperature T, and $\rho_w$ is a density of the water of the mixture of oil and water at the temperature T. The controller may further include a transmitter or transceiver for transmitting a signal representative of the fluid density of the mixture of oil and water, $\rho_m$, and the water cut, $\lambda$, to a remote user for display and/or further analysis thereof. Additionally, a flow meter may also be mounted within the substantially cylindrical conduit in the exit portion thereof. The flow meter directly measures a volumetric flow rate of the multi-phase fluid, and may be in communication with the controller for recordation and/or transmission of the volumetric flow rate for display and/or further analysis thereof.

These and other features of the present invention will become readily apparent upon further review of the following specification.

BRIEF DESCRIPTION OF THE DRAWINGS

Similar reference characters denote corresponding features consistently throughout the attached drawings.

Figure 1A:
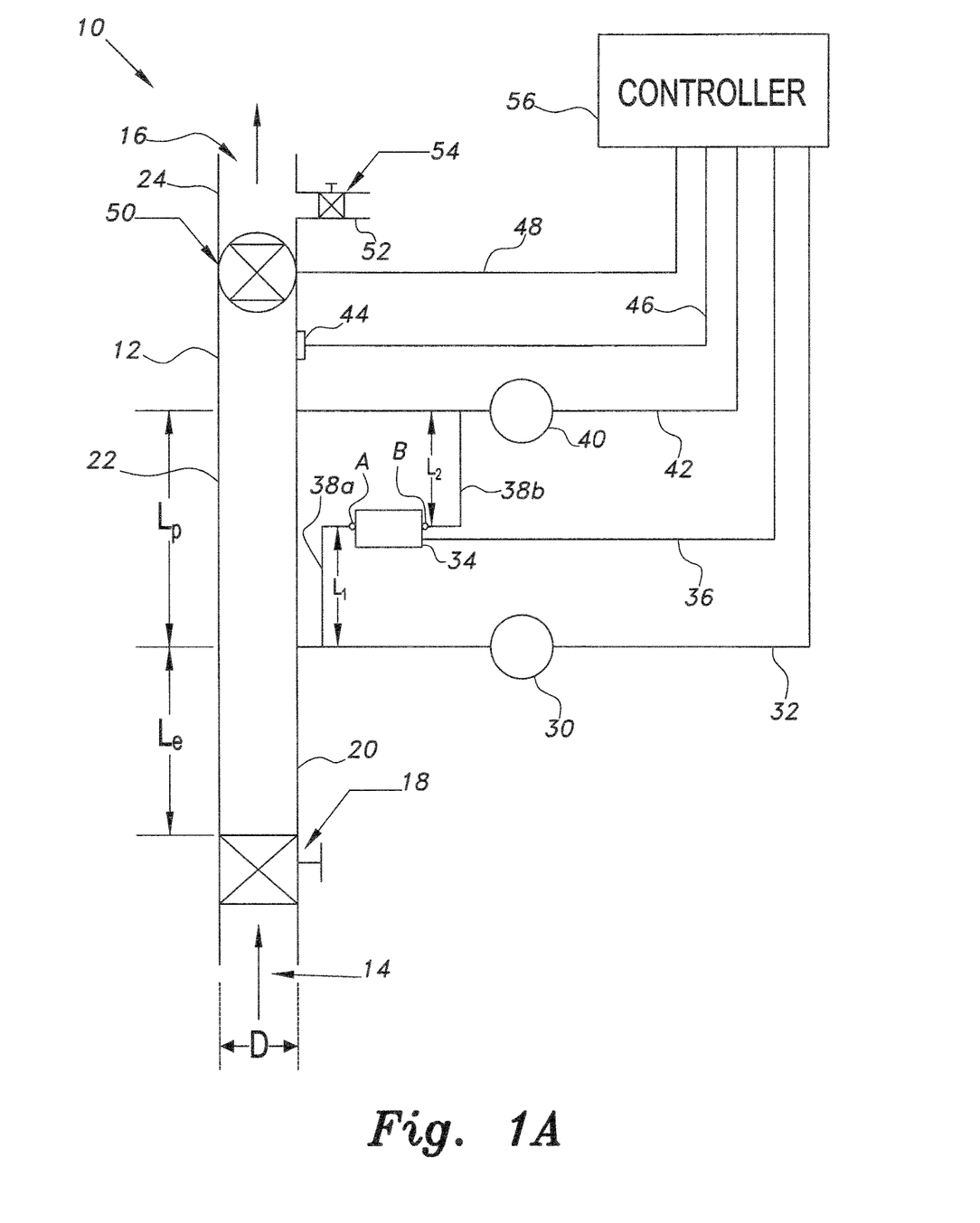
FIG. 1A is a schematic diagram illustrating a system for measuring multi-phase fluid flow characteristics according to the present invention.

The system for measuring multi-phase fluid flow characteristics 10 is an on-site system for measuring and calculating various characteristics of the multi-phase fluid flow, including the fluid density of the multi-phase fluid, $\rho_m$, such as a mixture of oil and water, as well as the water cut, $\lambda$, thereof. As shown in FIG. 1A, the system for measuring multi-phase fluid flow characteristics 10 includes a substantially cylindrical conduit 12 having a lower inlet 14 and an upper outlet 16. The lower inlet 14 is adapted for direct connection to an oil pipeline, an oil well, or the like for receiving the multi-phase fluid flowing therethrough.

As shown in FIG. 1A, the substantially cylindrical conduit 12 defines a diameter D and has an entrance portion 20 adjacent the lower inlet 14, an exit portion 24 adjacent the upper outlet 16, and a pressure monitoring portion 22 positioned therebetween. The entrance portion 20 has a length $L_e$ and the pressure monitoring portion 22 has a length $L_p$. An inlet valve 18 may be mounted within the entrance portion 20 adjacent the inlet 14 for selectively controlling fluid flow into the substantially cylindrical conduit 12. Additionally, as shown in FIG. 1A, a fluid sampling port 52 may be provided adjacent the outlet 16, allowing for manual sampling of the fluid to take place. As shown, the fluid sampling port 52 may be selectively manually sealed by a manual valve 54 or the like. The fluid sampling port 52 allows for offline determination of physical properties of the oil in the multi-phase fluid mixture. It should be understood that the overall dimensions and configuration of the conduit 12, as well as the positioning and relative dimensions of the fluid sampling port 52, may vary, depending upon the particular source of the multi-phase fluid (i.e., to match a particular pipeline, oil well, oil reservoir or the like).

A first gauge pressure transmitter 30 is connected to the substantially cylindrical conduit 12 at a boundary between the entrance portion 20 and the pressure monitoring portion 22, such that the first gauge pressure transmitter 30 measures a first gauge pressure $GP_1$ of the mixture of oil and water flowing through the substantially cylindrical conduit 12 and transmits it to a controller 56. A second gauge pressure transmitter 40 is connected to the substantially cylindrical conduit 12 at a boundary between the pressure monitoring portion 22 and the exit portion 24, such that the second gauge pressure transmitter 40 measures a second gauge pressure $GP_2$ of the mixture of oil and water flowing through the substantially cylindrical conduit 12 and transmits it to the controller 56, It should be understood that it is the length $L_p$ of the pressure monitoring portion 22 that contributes to the desired calculations.

A differential pressure transmitter 34 is in communication with the conduit 12 at the boundaries of the pressure measuring portion 22 by respective first and second impulse lines 38a, 38b (small bore pipes connecting the conduit 12 to the differential pressure transmitter 34). The differential pressure transmitter 34 measures the frictional pressure differential, $DP_f$, over the same length as the first and second gauge pressure transmitters 30, 40, while the total pressure differential, $DP_T$, is simply the difference between gauge pressure measurements, i.e., $DP_T=GP_1-GP_2$. With reference to FIG. 1A, the frictional pressure differential, $DP_f$, is the measured pressure differential between points A and B on either side of differential pressure transmitter 34, where point A is at a height $L_1$ from the lower boundary of the pressure monitoring portion 22 and point B is at a distance $L_2$ from the upper boundary of the pressure monitoring portion 22, as shown, i.e., $L_1$ and $L_2$ are both equal to one-half the length $L_p$ of the pressure monitoring portion 22. The lengths $L_1$ and $L_2$ of the impulse lines 38a and 38b and positioning of the measuring points A and B at a height midway between the upper and lower boundaries of the pressure monitoring portion are important for accurate functioning of the differential pressure transmitter 34. The differential pressure between points A and B measured by differential pressure transmitter 34, $DP_{AB}$, is given by $DP_{AB}=p_A-p_B$, where $p_A$ is the fluid pressure at point A, and $p_B$ is the fluid pressure at point B.

It will be understood that the first and second gauge transmitters 30, 40 and the pressure differential transmitter 34 each comprise a transducer for generating an electrical signal corresponding to gauge pressure or differential pressure drop, respectively, and circuitry for amplifying the signals and transmitting the signals, either by wired connection or wirelessly, to a controller 56, where the signals are processed as described herein.

The respective pressures $p_A$ and $p_B$ are given by $p_A=GP_1-\rho_m g L_1$ and $p_B=GP_2+\rho_m g L_2$, where $\rho_m$ is the fluid density of the mixture of oil and water and g is the gravitational acceleration constant near the Earth's surface (i.e., 9.8 m/s$^2$). Therefore, $p_A-p_B=(GP_1-GP_2)-\rho_m g(L_1+L_2)$. Since $L_1+L_2=L_p$, $p_A-p_B=(GP_1-GP_2)-\rho_m g L_p$, or $DP_{AB}=DP_T-\rho_m g L_p$.

The total pressure drop, $DP_T$, is the sum of the pressure drop due to gravity, $DP_G$, and the pressure drop due to friction in the conduit, $DP_f$, i.e., $DP_T=DP_G+DP_f$. The gravitational contribution is simply $DP_G=\rho_m g L_p$, so that $DP_{AB}=DP_T-DP_G$, or $DP_T=DP_{AB}+DP_G=DP_G+DP_f$. Thus, one can readily see that $DP_{AB}=DP_f$. Thus, the differential pressure transmitter 34 can directly measure the frictional pressure differential by calculating $DP_{AB}=p_A-p_B=DP_f$. It is important to note that the above shows that the frictional pressure differential is measured and calculated directly by the differential pressure transmitter 34 and its respective impulse lines 38a, 38b.

A temperature sensor 44 may be mounted within the substantially cylindrical conduit 12 in the exit portion 24 for measuring the temperature, T, of the multi-phase fluid. It should be understood that any suitable type of temperature sensor may be utilized, such as a resistance thermometer, thermocouple or the like. The first gauge pressure transmitter 30, the second gauge pressure transmitter 40, the differential pressure transmitter 34, and the temperature sensor 44 are each in communication with a controller 56, as shown.

When the substantially cylindrical conduit 12 is positioned vertically, as in FIG. 1A, the controller 56 calculates the fluid density of the mixture of oil and water, $\rho_m$, as $\rho_m=(DP_T-DP_f)/(L_p g)$, where $DP_T=GP_1-GP_2$. In cases where the substantially cylindrical conduit 12 is positioned at an angle $\theta$ with respect to a horizontal surface (such as the ground), as in FIG. 1B, the density is calculated using the vertical component of the gravitational contribution, i.e., $\rho_m=(DP_T-DP_f)/(L_p g \sin \theta)$. Additionally, a flow meter 50 may also be mounted within the substantially cylindrical conduit 12 in the exit portion 24. The flow meter 50 directly measures a volumetric flow rate of the multi-phase fluid, and may be in communication with the controller 56 for recordation and/or transmission of the volumetric flow rate for display and/or further analysis thereof. It should be understood that any suitable type of flow meter, such as a Venturi or liquid turbine flow meter, may be used.

The controller 56 further calculates the water cut, $\lambda$, as $\lambda=(\rho_m-\rho_o)/(\rho_w-\rho_o)$, where $\rho_o$ is the density of the oil of the mixture of oil and water at the temperature T, and $\rho_w$ is the density of the water of the mixture of oil and water at the temperature T. It should be understood that controller 56 may be a microcontroller located on site or remotely, or may take the form of any suitable computer system, such as that diagrammatically shown in FIG. 2. Data is received from lines 48, 46, 42, 36, 32, which are in respective communication with flow meter 50, temperature sensor 44, second gauge pressure transmitter 40, differential pressure transmitter 34, and first gauge pressure transmitter 30. It should be understood that data may be transmitted either through wired connection or wirelessly. The data received by controller 56 may be stored in memory 60, which may be any suitable type of computer readable and programmable memory and is preferably a non-transitory, computer readable storage medium. Calculations are performed by processor 58, which may be any suitable type of computer processor. The controller 56 may further include a transmitter or transceiver 62 for transmitting a signal representative of the fluid density of the mixture of oil and water, $\rho_m$, the water cut, $\lambda$, and the measured volumetric flow rate to a remote user for display and/or further analysis thereof.

Figure 2:
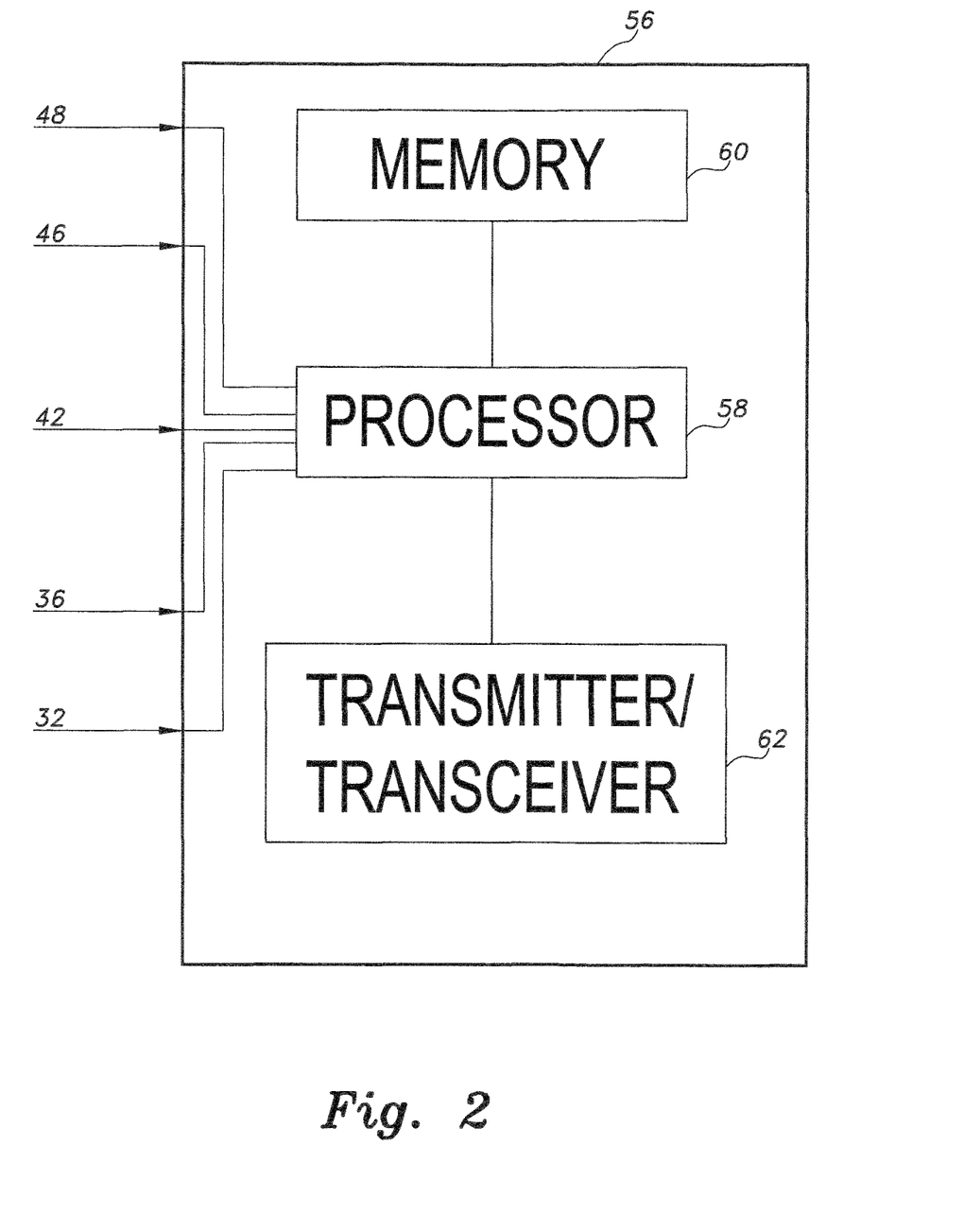
FIG. 2 is a block diagram illustrating sub-components of a controller circuit of the system of FIG. 1A.

Processor 58 may be associated with, or incorporated into, any suitable type of computing device, for example, a personal computer or a programmable logic controller. The processor 58, the memory 60, the transmitter/transceiver 62 and any associated computer readable recording media are in communication with one another by any suitable type of data bus, as is well known in the art.

Examples of computer-readable recording media include non-transitory storage media, a magnetic recording apparatus, an optical disk, a magneto-optical disk, and/or a semiconductor memory (for example, RAM, ROM, etc.). Examples of magnetic recording apparatus that may be used in addition to memory 60, or in place of memory 60, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW. It should be understood that non-transitory computer-readable storage media include all computer-readable media, with the sole exception being a transitory, propagating signal.

As can be seen from the above calculations, the system for measuring multi-phase fluid flow characteristics 10 can accurately measure the fluid mixture properties independent of pipe roughness and fluid mixture viscosity. It should be understood that the system for measuring multi-phase fluid flow characteristics 10 can be used on the surface (such as through connection with oil wells) or for down-hole monitoring of different fluid properties.

Figure 1B:
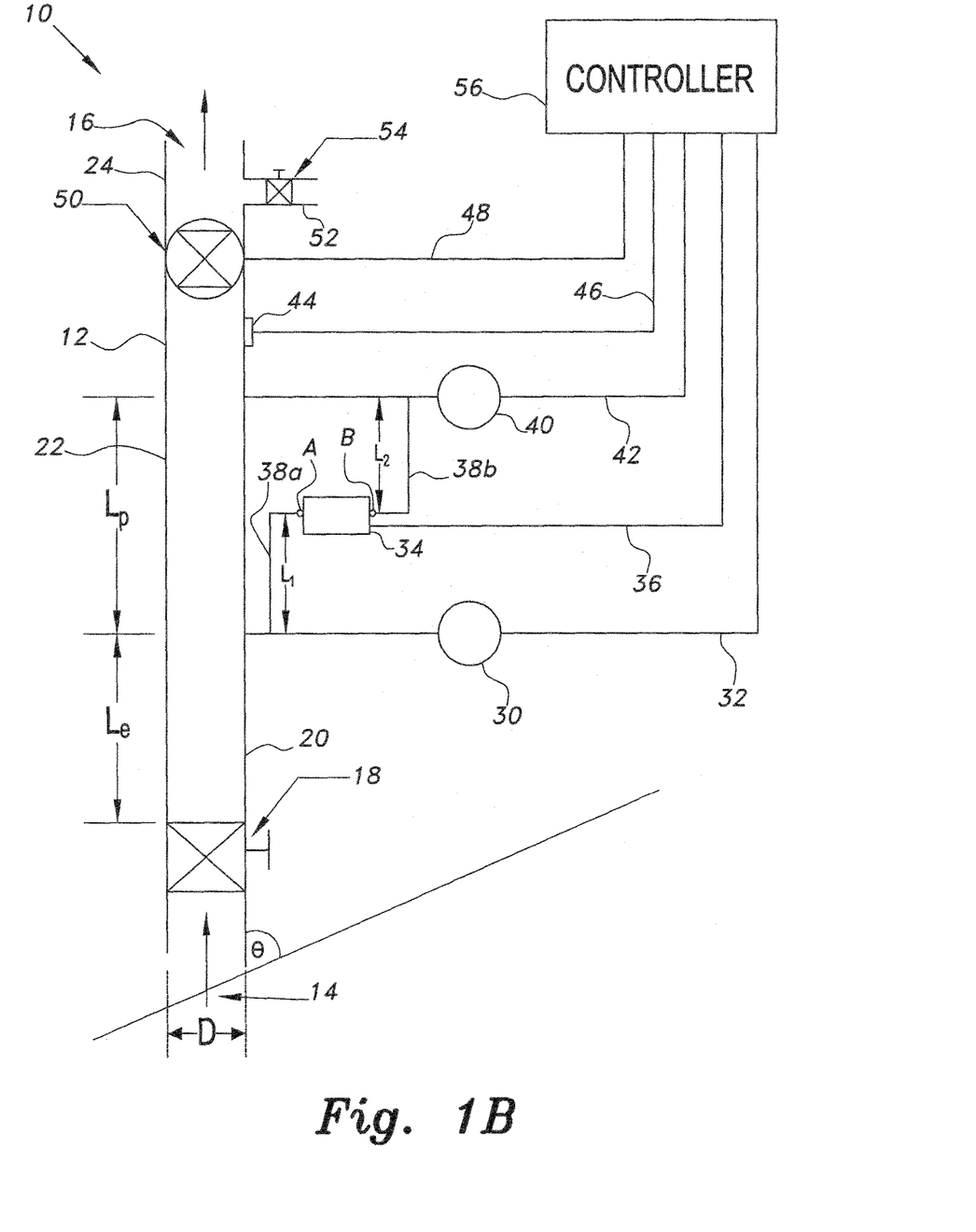
FIG. 1B is a schematic diagram illustrating the system of FIG. 1A inclined at an angle $\theta$ with respect to the horizontal.

As noted above, the system for measuring multi-phase fluid flow characteristics 10 may be used with any suitable type of pipe or conduit, i.e., the conduit is not limited to the exemplary linearly extending, cylindrical conduit 12 of FIGS. 1A and 1B.

Figure 3:
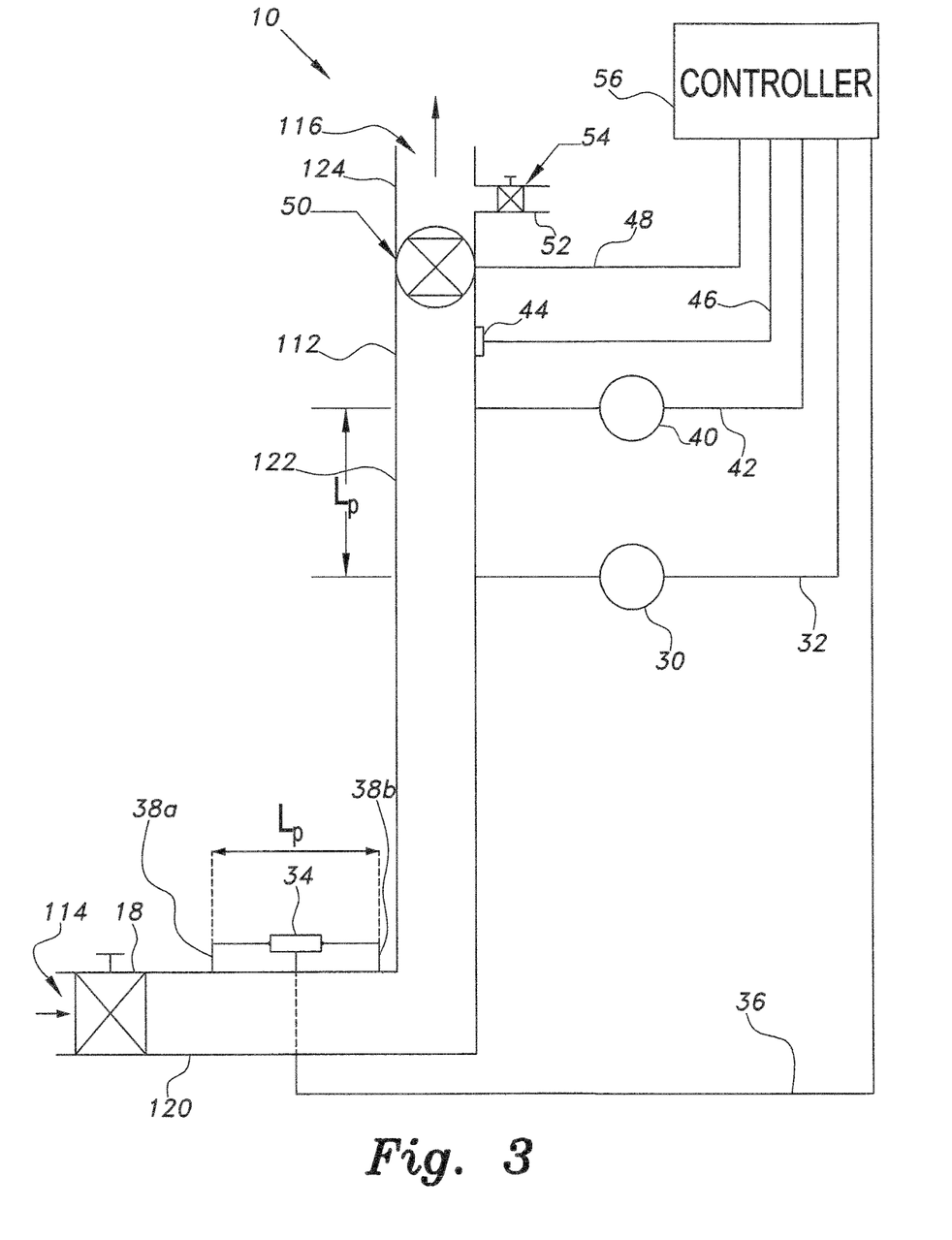
FIG. 3 is a schematic diagram illustrating an alternative embodiment of a system for measuring multi-phase fluid flow characteristics according to the present invention.

FIG. 3 shows an alternative configuration of the system for measuring multi-phase fluid flow characteristics 10 applied to an exemplary L-shaped conduit and operates in a similar manner. In FIG. 3, the L-shaped conduit 112 has a lower inlet 114 and an upper outlet 116. The lower inlet 114 is adapted for direct connection to an oil pipeline, an oil well, or the like for receiving the multi-phase fluid flowing therethrough, and is associated with a horizontally extending lower entrance portion 120. The exit portion 124 (adjacent upper outlet 116) and the pressure monitoring portion 122 are similar to their corresponding portions in the linearly extending, cylindrical conduit 12 of FIGS. 1A and 1B, and lower entrance portion 120 is similar to the entrance portion 20 in the conduit 12 of FIGS. 1A and 1B. However, as shown, the lower entrance portion 120 is arranged horizontally, thus forming an overall L-shaped conduit.

In the embodiment of FIG. 3, the gauge pressure transmitters 30, 40 operate in a manner similar to that described above. However, the differential pressure transmitter 34 has been moved to take differential pressure readings from the horizontally extending lower entrance portion 120. In order to utilize the same calculations described above with regard to the frictional pressure differential, the impulse lines 38a, 38b are spaced apart from one another by length $L_p$, thus matching the spacing of gauge pressure transmitters 30, 40. This allows for identical operation of the system for measuring multi-phase fluid flow characteristics 10 when applied to the L-shaped conduit 112 of FIG. 3 to that described above for the linearly extending, cylindrical conduit 12 of FIGS. 1A and 1B, except that the differential pressure transmitter 34 does not have to be positioned between the upper and lower boundaries of the gauge pressure transmitters 30, 40, since the lower impulse line 38a is at the same height as the upper impulse line 38b.

Figure 4:
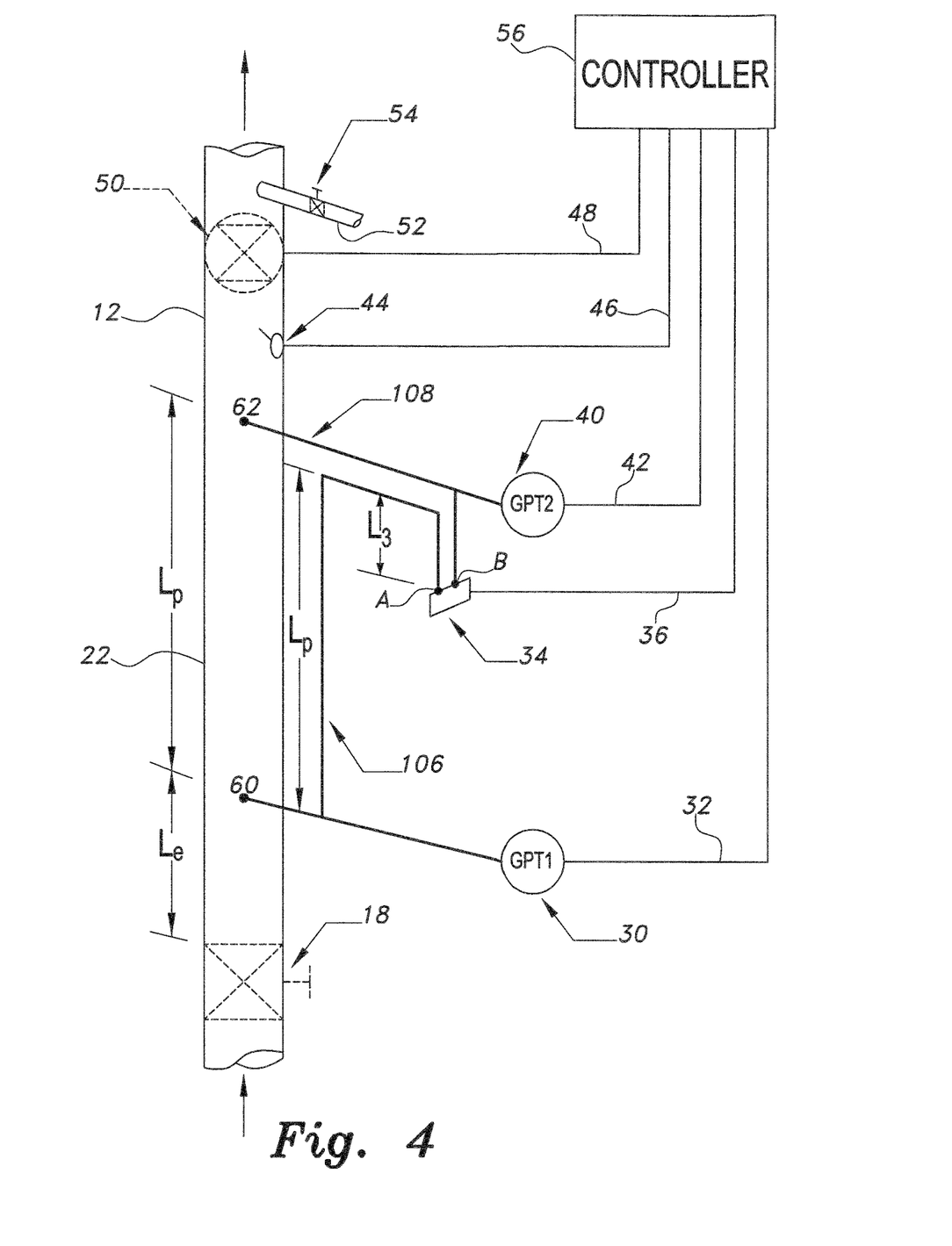
FIG. 4 is a schematic diagram illustrating an alternative embodiment of a system for measuring multi-phase fluid flow characteristics according to the present invention, showing another configuration of the impulse lines to the differential pressure transmitter.

FIG. 4 shows another configuration of the system similar to FIG. 1A, except for positioning and length of the impulse lines. In FIG. 4, the lower impulse line 106 taps into the conduit at a point 60 at the same height as the lower boundary of the pressure monitoring portion 22, and the upper impulse line 108 taps into the conduit at a point 62 at the same height as the upper boundary of the pressure monitoring portion 22. The lower impulse line extends from the conduit horizontally, then has a riser portion that extends vertically to the same height as the upper impulse line 108. Both impulse lines then extend horizontally parallel to each other at the height of the upper boundary of the pressure monitoring portion 22, then descend parallel to each other an equal distance $L_3$ to connect to ports on the differential pressure transmitter 34.

In this configuration, the differential pressure between the ports A and B of the differential pressure transmitter 34 is given by:

$$DP_{AB} = p_A - p_B \quad (1)$$

The equations for pressure at ports A and B can be written as:

$$p_A = GP_1 - \rho_m g L_p + \rho_m g L_3 \text{ and} \quad (2)$$

$$p_B = GP_2 + \rho_m g L_3. \quad (3)$$

Then, subtracting equation (3) from equation (2) gives the following:

$$p_A - p_B = (GP_1 - GP_2) - \rho_m g L_p. \quad (4)$$

Since the total pressure drop ($DP_T$) across the length $L_p$ is the difference in the gauge pressures ($GP_1 - GP_2$), equation 4 can be rewritten as:

$$DP_{AB} = DP_T - \rho_m g L_p. \quad (5)$$

The total pressure drop ($DP_T$) between points 60 and 62 across the length $L_p$ is also the sum of the gravitational pressure drop ($DP_G$) plus the frictional pressure drop ($DP_f$) according to the equation:

$$DP_T = DP_G + DP_f. \quad (6)$$

Since the gravitational pressure loss across the length $L_p$ is given by:

$$DP_G = \rho_m g L_p, \quad (7)$$

equation (6) can be written as:

$$DP_T = \rho_m g L_p + DP_f \quad (8)$$

Substituting equation (8) into equation (5) provides:

$$DP_{AB} = \rho_m g L_p + DP_f - \rho_m g L_p, \text{ or} \quad (9)$$

$$DP_{AB}(\text{measured}) = DP_f. \quad (10)$$

Thus, the differential pressure, $DP_{AB}$, measured by the differential pressure transmitter 34 is also the frictional pressure drop between pipe locations 60 and 62 for the impulse line configuration shown in FIG. 4.

It is to be understood that the present invention is not limited to the embodiments described above, but encompasses any and all embodiments within the scope of the following claims.

We claim:

1. A system for measuring multi-phase fluid flow characteristics, comprising:
   a substantially cylindrical conduit having a lower inlet and an upper outlet, an entrance portion adjacent the lower inlet, an exit portion adjacent the upper outlet, and a pressure monitoring portion positioned therebetween, the pressure monitoring portion having an upper boundary, a lower boundary, and a length $L_p$ extending between the upper boundary and the lower boundary, the substantially cylindrical conduit being oriented vertically;
   a first gauge pressure transmitter connected to the substantially cylindrical conduit at the lower boundary between the entrance portion and the pressure monitoring portion, the first gauge pressure transmitter measuring a first gauge pressure $GP_1$ of a multi-phase fluid flowing through the substantially cylindrical conduit;
   a second gauge pressure transmitter connected to the substantially cylindrical conduit at the upper boundary between the pressure monitoring portion and the exit portion, the second gauge pressure transmitter measuring a second gauge pressure $GP_2$ of the multi-phase fluid flowing through the substantially cylindrical conduit;
   a differential pressure transmitter having first and second ports;
   a first impulse line connecting the first port of the differential pressure transmitter to the conduit at the lower boundary of the pressure monitoring portion;
   a second impulse line connecting the second port of the differential pressure transmitter to the conduit at the upper boundary of the pressure monitoring portion, the differential pressure transmitter measuring frictional pressure differential, $DP_f$, between the upper and lower boundaries of the pressure monitoring portion over the length $L_p$;
   a temperature sensor mounted within the substantially cylindrical conduit in the exit portion thereof for measuring a temperature, T, of the multi-phase fluid; and
   a controller in communication with the first gauge pressure transmitter, the second gauge pressure transmitter, the differential pressure transmitter, and the temperature sensor, the controller having:
      means for calculating total pressure differential, $DP_T$, over the length $L_p$ of the pressure monitoring portion as $DP_T = GP_1 - GP_2$;
      means for calculating fluid density, $\rho_m$, of the multi-phase fluid as $\rho_m = (DP_T - DP_f)/L_p g$, wherein g is the gravitational acceleration constant; and
      when the multi-phase fluid is a mixture of oil and water, means for calculating water cut, $\lambda$, of the multi-phase fluid as $\lambda = (\rho_m - \rho_o)/(\rho_w - \rho_o)$, wherein $\rho_o$ is the density of the oil at the temperature T and $\rho_w$ is the density of the water at the temperature T.

2. The system for measuring multi-phase fluid flow characteristics as recited in claim 1, further comprising a fluid sampling port adjacent the outlet.

3. The system for measuring multi-phase fluid flow characteristics as recited in claim 2, further comprising an inlet valve positioned in the entrance portion of the substantially cylindrical conduit adjacent the inlet.

4. The system for measuring multi-phase fluid flow characteristics as recited in claim 1, further comprising a flow meter mounted within the substantially cylindrical conduit in the exit portion thereof, the flow meter measuring volumetric flow rate of the multi-phase fluid.

5. The system for measuring multi-phase fluid flow characteristics as recited in claim 1, wherein the controller comprises a microcontroller.

6. A system for measuring multi-phase fluid flow characteristics, comprising:
   a substantially cylindrical conduit having a lower inlet and an upper outlet, an entrance portion adjacent the lower inlet, an exit portion adjacent the upper outlet, and a pressure monitoring portion positioned therebetween, the pressure monitoring portion having an upper boundary, a lower boundary, and a length $L_p$ extending between the upper boundary and the lower boundary, the substantially cylindrical conduit being positioned at an angle $\theta$ with respect to horizontal;
   a first gauge pressure transmitter connected to the substantially cylindrical conduit at the lower boundary between the entrance portion and the pressure monitoring portion, the first gauge pressure transmitter measuring a first gauge pressure $GP_1$ of a multi-phase fluid flowing through the substantially cylindrical conduit;
   a second gauge pressure transmitter connected to the substantially cylindrical conduit at the upper boundary between the pressure monitoring portion and the exit portion, the second gauge pressure transmitter measuring a second gauge pressure $GP_2$ of the multi-phase fluid flowing through the substantially cylindrical conduit;
   a differential pressure transmitter having first and second ports;
   a first impulse line connecting the first port of the differential pressure transmitter to the conduit at the lower boundary of the pressure monitoring portion;
   a second impulse line connecting the second port of the differential pressure transmitter to the conduit at the upper boundary of the pressure monitoring portion, the differential pressure transmitter measuring frictional pressure differential, $DP_f$, between the upper and lower boundaries of the pressure monitoring portion over the length $L_p$;
   a temperature sensor mounted within the substantially cylindrical conduit in the exit portion thereof for measuring a temperature, T, of the multi-phase fluid; and
   a controller in communication with the first gauge pressure transmitter, the second gauge pressure transmitter, the differential pressure transmitter, and the temperature sensor, the controller having:
      means for calculating total pressure differential, $DP_T$, over the length $L_p$ of the pressure monitoring portion as $DP_T = GP_1 - GP_2$;
      means for calculating fluid density of the multi-phase fluid, $\rho_m$, as $\rho_m = (DP_T - DP_f)/(L_p g \sin \theta)$, wherein g is the gravitational acceleration constant; and
      when the multi-phase fluid is a mixture of oil and water, means for calculating water cut, $\lambda$, of the multi-phase fluid as $\lambda = (\rho_m - \rho_o)/(\rho_w - \rho_o)$, wherein $\rho_o$ is the density of the oil at the temperature T and $\rho_w$ is the density of the water at the temperature T.

7. The system for measuring multi-phase fluid flow characteristics as recited in claim 6, further comprising a fluid sampling port adjacent the outlet.

8. The system for measuring multi-phase fluid flow characteristics as recited in claim 7, further comprising an inlet valve positioned in the entrance portion of the substantially cylindrical conduit adjacent the inlet.

9. The system for measuring multi-phase fluid flow characteristics as recited in claim 6, further comprising a flow meter mounted within the substantially cylindrical conduit in the exit portion thereof, the flow meter measuring volumetric flow rate of the multi-phase fluid.

10. The system for measuring multi-phase fluid flow characteristics as recited in claim 6, wherein the controller comprises a microcontroller.

11. A system for measuring multi-phase fluid flow characteristics, comprising:

a substantially L-shaped conduit having a horizontal pipe and a vertical pipe extending from the horizontal pipe, a lower inlet in the horizontal pipe and an upper outlet in the vertical pipe, a horizontally extending entrance portion adjacent the lower inlet, a vertically extending exit portion adjacent the upper outlet, an elongated vertically extending gauge pressure monitoring portion in the vertical pipe defining a length $L_p$, and an elongated horizontally extending pressure differential pressure monitoring portion in the horizontal pipe defining a length $L_p$ equal in length to the length of the gauge pressure monitoring portion;

a first gauge pressure transmitter connected to the vertical pipe at the lower end of the gauge pressure monitoring portion, the first gauge pressure transmitter measuring a first gauge pressure $GP_1$ of a multi-phase fluid flowing through the L-shaped conduit;

a second gauge pressure transmitter connected to the vertical pipe at the upper end of the gauge pressure monitoring portion, the second gauge pressure transmitter measuring a second gauge pressure $GP_2$ of the multi-phase fluid flowing through the L-shaped conduit a distance $L_p$ from the lower end;

a differential pressure transmitter having first and second ports;

a first impulse line connecting the first port of the differential pressure transmitter to the horizontal pipe at an inner end of the differential pressure monitoring portion;

a second impulse line connecting the second port of the differential pressure transmitter to the horizontal pipe at an outer end of the differential pressure monitoring portion, the differential pressure transmitter measuring frictional pressure differential, $DP_f$, between the inner and outer ends of the differential pressure monitoring portion over the length $L_p$;

a temperature sensor mounted within the vertical pipe in the exit portion thereof for measuring a temperature, T, of the multi-phase fluid; and a controller in communication with the first gauge pressure transmitter, the second gauge pressure transmitter, the differential pressure transmitter, and the temperature sensor, the controller having:

means for calculating total pressure differential, $DP_T$, over the length $L_p$ of the gauge pressure monitoring portion as $DP_T = GP_1 - GP_2$;

means for calculating fluid density, $\rho_m$, of the multi-phase fluid as $\rho_m = (DP_T - DP_f)/L_p g$, wherein g is the gravitational acceleration constant; and when the multi-phase fluid is a mixture of oil and water, means for calculating water cut, $\lambda$, of the multi-phase fluid as $\lambda = (\rho_m - \rho_o)/(\rho_w - \rho_o)$, wherein $\rho_o$ is the density of the oil at the temperature T and $\rho_w$ is the density of the water at the temperature T.

12. The system for measuring multi-phase fluid flow characteristics as recited in claim 11, further comprising a fluid sampling port adjacent the outlet.

13. The system for measuring multi-phase fluid flow characteristics as recited in claim 12, further comprising an inlet valve positioned in the horizontally extending entrance portion of the substantially L-shaped conduit adjacent the inlet.

14. The system for measuring multi-phase fluid flow characteristics as recited in claim 11, further comprising a flow meter mounted within the substantially L-shaped conduit in the vertically extending exit portion thereof, the flow meter measuring a volumetric flow rate of the multi-phase fluid.

15. The system for measuring multi-phase fluid flow characteristics as recited in claim 11, wherein the controller comprises a microcontroller.

* * * * *